United States Patent [19]

Schmidlin

[11] Patent Number: 4,607,028
[45] Date of Patent: Aug. 19, 1986

[54] NOVEL CARBOXYLIC ACID ESTERS
[75] Inventor: Julius Schmidlin, Basel, Switzerland
[73] Assignee: Ciba-Geigy Corporation, Ardsley, N.Y.
[21] Appl. No.: 639,033
[22] Filed: Aug. 9, 1984
[30] Foreign Application Priority Data Aug. 18, 1983 [CH] Switzerland .................. 4512/83

[51] Int. Cl.$^4$ ............................................. A61K 31/56
[52] U.S. Cl. ................................. 514/180; 260/397.1
[58] Field of Search ...................................... 260/397.1

[56] References Cited

U.S. PATENT DOCUMENTS 4,285,937 8/1981 Kalvoda .......................... 260/397.1

Primary Examiner—Elbert L. Roberts
Attorney, Agent, or Firm—Michael W. Glynn

[57] ABSTRACT

Novel 17β-methoxycarbonyl derivatives of the androstane series of the formula

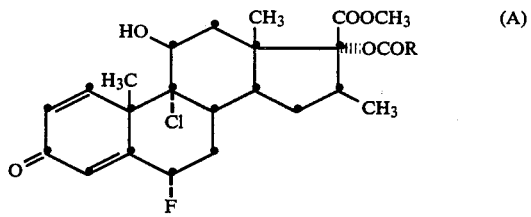

in which R represents alkyl having from 1 to 4 carbon atoms are distinguished by a high local anti-inflammatory activity without having any systemic side effects. The compounds are manufactured by conventional processes of steroid chemistry.

7 Claims, No Drawings

NOVEL CARBOXYLIC ACID ESTERS

The present invention relates to novel steroidal carboxylic acid esters, especially methyl esters of 17β-carboxylic acids of the androstane series corresponding to the formula

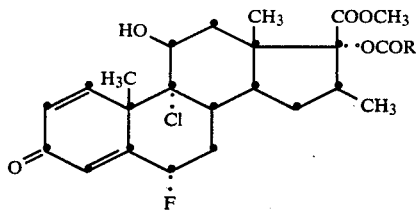

in which R represents alkyl having from 1 to 4 carbon atoms, and to processes for the manufacture thereof, also to pharmaceutical compositions containing those compounds and to processes for the manufacture thereof.

The alkyl identified by the symbol R is preferably linear, such as methyl, propyl, butyl and, above all, ethyl.

Among these compounds, special emphasis is to be given to methyl esters of 9α-chloro-6α-fluoro-11β-hydroxy-16β-methyl-3-oxo-17α-acetoxyandrosta-1,4-diene-17β-carboxylic acid and 9α-chloro-6α-fluoro-11β-hydroxy-16β-methyl-3-oxo-17α-valeryloxyandrosta-1,4-diene-17α-carboxylic acid, and, above all, the 9α-chloro-6α-fluoro-11β-hydroxy-16β-methyl-3-oxo-17α-propionyloxyandrosta-1,4-diene-17β-carboxylic acid methyl ester of the formula

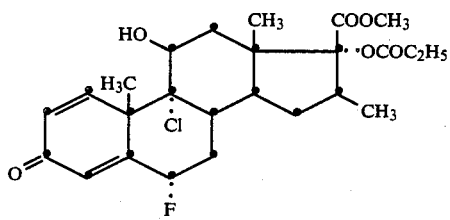

Esters of poly-halogenated androsta-1,4-dien-3-one-17β-carboxylic acids have been described. For example U.S. Pat. Specification No. 4,285,937 relates to esters of mono-, di- and tri-hydric aliphatic alcohols with 11β,17α-dihydroxy-3-oxo-androsta-1,4-diene-17β-carboxylic acids in which the 17α-hydroxy is acylated by an aliphatic carboxylic acid having not more than 7 carbon atoms and in which chlorine or hydrogen is in the 2-position, chlorine or fluorine, independently of one another, is in the 6α- and/or 9α-position and α- or β-oriented methyl or, alternatively, methylene is in the 16-position. The compounds of the present invention can also be classified under this broad general scope, although they have not been considered in detail in any other respect and the patent specification relates primarily to a differently substituted group of compounds. In the above case (see claims 15 and 16 of the U.S. Patent Specification), special emphasis is given to lower alkyl esters of acids that have as specific feature 16α-methyl and as further features a 17α-hydroxy group acylated by lower alkanoyl, and a 6α-fluorine and a 9α-chlorine and in which the 2-position is unsubstituted. Owing to their special activity, the following compounds are specifically mentioned (see column 2, lines 32-41 of the above-mentioned U.S. Patent Specification): 2-chloro-6α,9α-difluoro-11β-hydroxy-17α-propionyloxy-16α-methyl-3-oxo-androsta-1,4-diene-17β-carboxylic acid methyl ester, 2,9α-dichloro-6α-fluoro-11β-hydroxy-17β-propionyloxy-16α-methyl-3-oxo-androsta-1,4-diene-17β-carboxylic acid methyl ester and also 9α-chloro-6α-fluoro-11β-hydroxy-17α-propionyloxy-16α-methyl-3-oxo-androsta-1,4-diene-17β-carboxylic acid methyl ester (0) which is free of chlorine in the 2-position. No special advantages were indicated for the remaining two compounds mentioned in the U.S. Patent Specification, that is 2-chloro-9α-fluoro-11β-hydroxy-17α-propionyloxy-16β-methyl-3-oxo-androsta-1,4-diene-17β-carboxylic acid methyl ester and 2,9α-dichloro-6α-fluoro-11β-hydroxy-17α-propionyloxy-16α-methyl-3-oxo-androsta-1,4-diene-17β-carboxylic acid chloromethyl ester. It is reported in the U.S. Patent Specification mentioned that the esters disclosed therein have a high anti-inflammatory activity (for example in the foreign body granuloma test in rats they exhibit a pronounced anti-inflammatory action in a dosage range of approximately 0.001–0.03 mg per cotton wool pellet); during the same administration, however, they acted on the thymus, adrenal glands and body weight, but only at doses of 0.3 mg and above per cotton wool pellet. The compounds of the patent specification mentioned also proved especially effective in the rat-ear test according to Tonnelli.

Despite the substantially lower systemic activity which has been achieved with the tested compounds of the U.S. Patent Specification mentioned in comparison with the known active substances, the search for topically highly active corticoids which, however, had the smallest possible systemic activity or even no systemic activity, even in the case of relatively long administration, remained one of the most pressing tasks in this field. Although the 16α-methyl compounds given special emphasis proved satisfactory in the test procedures used, they were unable to satisfy more stringent demands, especially in the case of direct testing of their systemic effects.

Surprisingly, it has now been found that a small selection of compounds that has not previously been considered and that is characterised above all by β-orientation of the 16-methyl and is distinguished by a surprisingly low systemic activity stands out from the generally categorised, broad class of compounds of the U.S. Patent Specification under discussion, as can be demonstrated by the following tables of data:

TABLE 1

| Cotton wool pellet granuloma test (rat) local | | | | | |
|---|---|---|---|---|---|
| | | inhibition or reduction ($ED_{20-30}$ in μg per pellet) | | | |
| compound | granuloma | contralateral granuloma | adrenal glands | thymus | body weight |
| I | 0.2 | 125 ∅* | 125 ∅ | 125 ∅ | 125 ∅ |
| 0 | 0.2 | 125 ∅ | 125 ∅ | 125 ∅ | 125 ∅ |

*∅ = without effect at the dose indicated

TABLE 2

| Cotton wool pellet granuloma test (rat) peroral | | | | |
|---|---|---|---|---|
| | | inhibition or reduction ($ED_{20-30}$ in mg per kg animal) | | |
| compound | granuloma | adrenal glands | thymus | body weight |
| I | 3 ∅* | 3 ∅ | 3 ∅ | 3 ∅ |

TABLE 2-continued

| | Cotton wool pellet granuloma test (rat) peroral | | | |
| --- | --- | --- | --- | --- |
| | inhibition or reduction ($ED_{20-30}$ in mg per kg animal) | | | |
| compound | granuloma | adrenal glands | thymus | body weight |
| 0 | 3 | 3 | 1 | 3 |

*0 = without effect at the dose indicated

TABLE 3

| | Liver glycogen test (rat) subcutaneous Tryptophanpyrrolase test (rat) subcutaneous | |
| --- | --- | --- |
| compound | glycogen formation ($ED_{20-30}$ in mg per kg animal) | induction of tryptophanpyrrolase ($ED_{20}$ in mg per kg animal) |
| I | >10 | >3 |
| 0 | 1 | 0.1–0.3 |

According to Table 1, when administered topically, the 16β-methyl compound (I) has a strong anti-inflammatory action which equals that of the corresponding 16α-methyl compound (0). The 16β-methyl compound (I) mentioned differs, however, as can be seen from Table 2, advantageously from the 16α-methyl compound (0) in that it does not influence the thymus, adrenal glands and body weight when administered perorally at the tested dosage. The finding to be seen in Table 3 according to which after subcutaneous administration to rats the 16β-methyl compound (I) according to the invention brings about no significant increase in liver glycogen, even at high doses, in contrast to the 16α-methyl compound (0), supports the extensive lack of corticosteroid-specific side effects. In keeping with this is the pronounced difference, also shown in Table 3, which is found for the above-mentioned pair of compounds (I) and (0) with regard to the induction of tryptophanpyrrolase. In this test, in comparison with the 16α-methyl compound (0), the 16β-methyl compound (I) according to the invention does not exhibit the effect specific to systemically active glucocorticoids, even at a dose that is from 10 to 30 times higher.

Owing to this surprising, experimentally proved absence of any systemic side effects together with full retention of the extraordinarily high local anti-inflammatory activity, the compounds of the formula (A) according to the invention are perfectly suitable not only as locally, above all topically, administrable antiphlogistic therapeutic agents for all indications for which corticoids are cutomary but, in addition, also for specific areas of use in which known corticoids often have serious disadvantages, for example for long-term therapy of refractory and/or recurrent skin disorders, such as psoriasis. Furthermore, the compounds according to the invention can be used for administration by inhalation for the therapeutic treatment of asthmatic conditions and symptoms.

The novel esters according to the invention of the formula (A) characterised above can be manufactured in a manner known per se, especially by (a) treating a 9β,11β-oxo compound of the formula

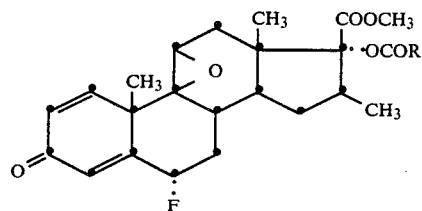

in which R has the meaning given above with hydrogen chloride or with an agent yielding hydrogen chloride, or (b) adding elements of hypochlorous acid to a 9(11)-unsaturated compound of the formula

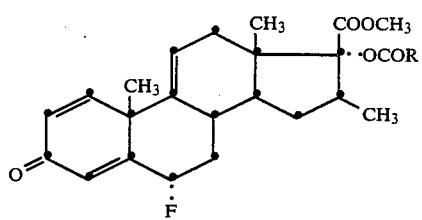

in which R has the meaning given above, or (c) dehydrogenating in the 1,2-position a 1,2-saturated compound of the formula

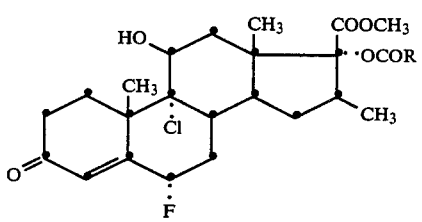

in which R has the meaning given above, or (d) esterifying a carboxylic acid of the formula

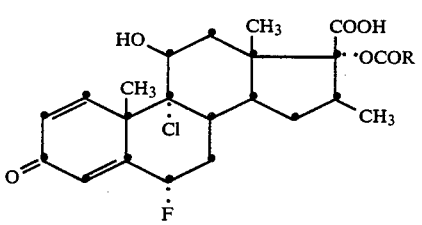

in which R has the meaning given above, or a salt or a reactive functional derivative thereof using a methylating agent, or (e) acylating 9α-chloro-6α-fluoro-11β,17α-dihydroxy-16β-methyl-3-oxoandrosta-1,4-diene-17β-carboxylic acid methyl ester of the formula

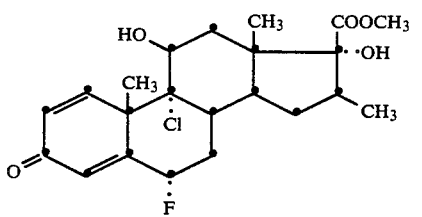

with a carboxylic acid of the formula R—COOH (VII) in which R has the meaning given above, or with a reactive functional derivative thereof, optionally while temporarily protecting the 11β-hydroxy, or (f) in a compound of the formula

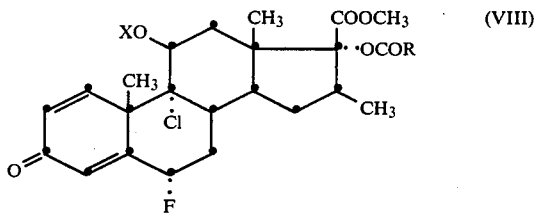

corresponding to the methyl ester of the formula (A) defined above and in which the 11β-hydroxy is protected and X represents a hydroxy-protecting group and R has the meaning given above, removing the protecting group X.

The cleaving according to the invention of the 9β,11β-oxido group in a starting material of the formula (II) according to process variant (a) by treatment with hydrogen chloride is carried out in a manner known per se, it being advantageous to use anhydrous hydrogen chloride, optionally in the presence of an inert solvent, such as chloroform, tetrahydrofuran or, especially, dimethylformamide.

Instead of the hydrogen halide itself, it is also possible to use an agent yielding hydrogen chloride, such as a salt thereof with a tertiary organic base, for example pyridine.

The starting materials of the formula II can be obtained in a manner known per se, for example by removing the elements of water from a 6α-fluoro-11β-hydroxy-16β-methyl-17α-OCOR-3-oxo-androsta-1,4-diene-17β-carboxylic acid methyl ester, for example by treatment with a suitable dehydrating agent, for example an acid chloride, such as phosphorus oxychloride or methanesulphonic acid chloride, in the presence of a base, for example pyridine, adding hypobromous acid (which, for example, is used in the form of N-bromoacetamide or N-bromosuccinimide in acidic medium) to the 9,11-double bond of the 6α-fluoro-16β-methyl-17α-OCOR-3-oxo-androsta-1,4,9(11)-triene-17β-carboxylic acid methyl ester so obtained and removing hydrogen bromide from the resulting 9α-bromo-11β-hydrine by treatment with a base, especially an alkali metal salt of a carboxylic acid, for example potassium acetate, or with an aprotic organic base, especially, for example, with 1,5-diazabicyclo[5.4.0]-undec-5-ene, with formation of the desired starting material of the formula II. Inorganic bases, such as alkali metal hydroxides or carbonates, for example sodium hydroxide or potassium carbonate, or alternatively alkali metal alkoxides, such as sodium methoxide or potassium tert.-butoxide, can be used to remove the hydrogen bromide; in this case, however, the 17α-alkanoyloxy group and the 17β-methoxycarbonyl group are at least partially hydrolysed to form the free hydroxy and carboxy group, respectively, and must subsequently be esterified, for example under the conditions of process variants (d) and (e) described below. In the above intermediates, R has the meaning given above. In an analogous manner, it is also possible to obtain the corresponding 1,2-saturated starting materials.

The addition according to the invention of elements of hypochlorous acid to the 9(11)-double bond of the starting material of the formula III according to process variant (b) is carried out in a manner known per se. The operation is carried out, for example, with aqueous hypochlorous acid or an agent yielding hypochlorous acid, such as an N-chlorocarboxylic acid amide or imide, for example N-chlorosuccinimide (see U.S. Pat. No. 3,057,886), can be used. The reaction is carried out in an inert solvent, such as a tertiary alcohol, for example tert.-butyl alcohol, an ether, for example diethyl ether, 1,2-dimethoxyethane, dioxan or tetrahydrofuran, or a ketone, for example acetone, in the presence of water and, optionally, an acid. It is also possible, however, to carry out the addition in a non-aqueous medium. In an especially advantageous embodiment, lower alkyl hypochlorites, especially tert.-butyl hypochlorite, are used in tert.-butyl alcohol or in an inert water-immiscible solvent, such as a nitrohydrocarbon, for example nitromethane, customarily in the presence of perchloric acid (see German Patent Specification No. 2 011 559).

The staring materials of the formula III or their 1,2-dihydro analogues can be manufactured in a manner known per se, for example by removing the elements of water from a 6α-fluoro-11β-hydroxy-16β-methyl-17α-OCOR-3-oxo-(androsta-1,4-diene or androst-4-ene)-17β-carboxylic acid methyl ester, for example by treatment with a suitable dehydrating agent, such as an acid chloride, for example phosphorus oxychloride or methanesulphonic acid chloride, in the presence of a base, for example pyridine. (In the above starting material R has the meaning given in the introduction).

The 1,2-dehydrogenation according to the invention in accordance with process variant (c) can be carried out in a manner known per se, for example by biological dehydrogenation processes, for example using the microorganisms Corynebacterium simplex or Septomyxa affinis or their enzyme systems, or using selenium dioxide in an organic solvent, for example tert.-butyl alcohol. Preferably, however, 2,3-dichloro-5,6-dicyano-1,4-benzoquinone is left to act, advantageously at temperatures of approximately from 40° C. to boiling heat, for several, for example 6–24, hours; there are used as reaction medium customary organic solvents, for example aromatic hydrocarbons, such as benzene or xylene, lower aliphatic alcohols, such as ethanol, propyl alcohol or tert.-butyl alcohol, lower aliphatic ketones, such as acetone or 2-butanone, aliphatic esters, such as ethyl acetate, or cyclic ethers, such as dioxan or tetrahydrofuran. All these variants are standard processes in steroid chemistry and are therefore generally known.

The starting materials of the formula IV can be obtained, for example, by adding elements of hypochlorous acid in the manner given under process variant (b) to a 6α-fluoro-16β-methyl-17α-OCOR-3-oxo-androsta-4,9(11)-diene-17β-carboxylic acid methyl ester (which can be obtained, for example, by removing the elements of water from a corresponding 6α-fluoro-(11α or 11β)-hydroxy-16β-methyl-17α-OCOR-3-oxo-androst-4-ene-17β-carboxylic acid methyl ester using methanesulphonyl chloride). (In these intermediates R has the meaning given in the introduction).

The esterification according to the invention (that is to say the conversion into the methyl ester) according to process variant (d) can be carried out in a manner known per se, advantageously by treating the free acid of the formula V with diazomethane. The reaction is carried out in an inert organic solvent, such as an aromatic hydrocarbon, for example benzene or toluene, a lower alkanol, for example preferably methanol, an ether, for example diethyl ether, 1,2-dimethoxyethane, tetrahydrofuran or dioxan, or a halogenated lower alkane, for example dichloromethane or chloroform, or a mixture of several such solvents, at a temperature of from approximately −10° to approximately +30°, diazomethane especially being added in portions to a solution of the acid (V) either in gaseous state (optionally using an inert propellant gas, such as argon or nitrogen) or in solution, for example in one of the solvents mentioned. An alternative method of esterification comprises treating the free acid in an inert organic solvent with an N,N'-disubstituted O-methylisourea at temperatures of from approximately 20° to approximately 100° C. In this operation the reagent can also be formed directly in the reaction medium by, for example, treating a methanolic solution of the free acid (V) with an N,N'-disubstituted carbodiimide, such as N,N'-dicyclohexyl carbodiimide. It is also possible to use conventional methods of esterification, such as treatment of the free acid (V) with an excess of methanol with acid catalysis (for example by sulphuric acid), treatment of an alkali metal salt, such as the sodium, potassium or lithium salt, of the acid (V) with a methyl ester of a strong acid, for example a methyl halide (such as methyl iodide or methyl bromide), dimethyl sulphate or an organic sulphonate (such as methyl-methanesulphonate or methyl-p-toluenesulphonate) or, alternatively, treatment of a mixed anhydride of the acid (V) with methanol optionally in the presence of a base, especially a tertiary organic base, such as a tertiary amine (for example triethylamine or N-methylmorpholine) or, especially, in the presence of pyridine or one of its homologues or in the presence of quinoline. The second acid component of the mixed anhydride of the acid (V) can be either an inorganic acid, such as, especially, hydrochloric acid (in which case the chloride of the acid V is present) or an organic acid, such as, especially, trifluoroacetic acid, or also a lower alkanecarboxylic acid, especially a lower alkanecarboxylic acid of the formula RCOOH in which R has the meaning given in the introduction. Such mixed anhydrides of the acid (V) with the organic acids mentioned can optionally be in the form of primary products in the reaction mixture which is obtained, for example, analogously to process variant (e) by acylating 6α-fluoro-9α-chloro-11β,17α-dihydroxy-16β-methyl-3-oxo-androsta-1,4-diene-17β-carboxylic acid (VIA) (or a derivative thereof that is protected at the 11β-hydroxy) with an anhydride of the formula (R—CO)₂O (VIIA) or R—CO—O—CO—CF₃ (VIIB) in which R has the meaning given in the introduction. The esterification according to the invention in accordance with process variant (d) is carried out subsequently by treating the crude reaction mixture with methanol which is preferably used in such an excess that the unused acylation reagent (VIIA or VIIB) can be destroyed at the same time. This esterification variant can be carried out with either acidic or basic catalysis.

Starting materials of the formula V can be obtained in a manner known per se, for example by oxidative sidechain degradation of a corresponding 21-hydroxy-20-ketone of the pregna series, that is to say a 6α-fluoro-9α-chloro-11β,21-dihydroxy-16β-methyl-17α-OCOR-pregna-1,4-diene-3,20-dione (IX) in which R has the meaning given above. The latter compounds, for their part, can, insofar as they are not known, be obtained in known manner from 6α-fluoro-9α-chloro-11β,17α,21-trihydroxy-16β-methylpregna-1,4-diene-3,20-dione (IXA) by converting the latter using a lower alkylorthoester of a carboxylic acid R—COOH (VII) into the corresponding 17α,21-orthoester of the above-mentioned triol (in which the third oxygen atom of this orthoester carries the original lower alkyl) and converting this orthoester into the desired 17-monoester by careful hydrolysis according to a conventional general process. The oxidative degradation of the hydroxyacetyl side chain of the compounds of the formula (IX) is carried out in a methodically optimised manner known per se using glycol-cleaving oxidising agents that are suitable for the purpose, such as, especially, periodic acid or salts thereof, advantageously organic salts that are formed in the reaction mixture by adding a base, such as pyridine. The reaction is advantageously carried out in the presence of water in a water-miscible organic solvent, such as a lower alkanol, for example methanol, ethanol, tert.-butyl alcohol or ethylene glycol monomethyl or monoethyl ether, or a cyclic ether, for example tetrahydrofuran. It is also possible to carry out the oxidation using a derivative of bismuth pentoxide, such as an alkali metal bismuthate, for example sodium or potassium bismuthate, preferably in acetic acid, and especially in aqueous acetic acid.

This oxidative degradation of the hydroxyacetyl side chain can also be used for the manufacture of starting materials of other process variants (for example a, b, c and e) by cleaving the side chain in a 21-hydroxy-20-oxo derivative that is analogous to the compound of the formula (IX) and is suitably substituted in the ring A or C and converting the resulting free 17β-carboxylic acid into the methyl ester under the conditions described above for process variant (d) according to the invention. Special mention should be made, for example, of derivatives that differ from pregnane compounds of the formula (IX) in the ring C by the 9β,11β-oxido group, the 9(11)-double bond or the protected 11β-hydroxy group and/or in the ring A by the saturated 1,2-bond. Using periodic acid or salts thereof it is also possible to oxidise in analogous manner the triol (IXA), or an analogue thereof that is protected at the 11β-hydroxy, to form 6α-fluoro-9α-chloro-11β,17α-dihydroxy-16β-methyl-3-oxo-androsta-1,4-diene-17β-carboxylic acid (VIA), or the 11-0-protected derivative thereof, which can be used as starting materials or intermediates in process variants (e) or (f) respectively.

The acylation according to the invention of the 17α-hydroxy in accordance with process variant (e) is carried out in a manner known per se by reacting the ester VI with the particular acid R—COOH (VII) or, preferably, with a functional derivative thereof, such as a halide, for example chloride, or especially an anhydride, for example a symmetrical anhydride of the formula (R—CO)₂O (VIIA) or a mixed anhydride of the type R—CO—O—COCF₃ (VIIB), R having the meaning given above. The acylation can also be carried out in the presence of an acidic catalyst, such as p-toluenesulphonic acid, sulphosalicylic acid, perchloric acid or an acidic ion exchanger of the type Amberlite (Registered Trademark) IR 120; there is customarily used as reaction medium in that operation a cyclic hydrocarbon, such as benzene or toluene, or a chlorinated aliphatic hydrocarbon, such as methylene chloride or chloroform. Advantageously, the operation is carried out with an excess of anhydride at temperatures of from approximately 20° to approximately 100° C. Acylation is carried out especially with basic catalysis, especially in the presence of a strong organic base, such as, preferably, 4-dimethylaminopyridine; it is advantageous to use as acylation agent a symmetrical anhydride (VIIA) and as solvent or diluent, for example, a heteroaromatic base, such as quinoline or pyridine or, preferably, the homologues thereof, and also cyclic ethers, such as tetrahydrofuran, or chlorinated aliphatic hydrocarbons, such as chloroform or methylene chloride; the reaction temperature is customarily in the range of from approximately 0° to approximately 50° C., advantageously room temperature or slightly below.

The starting material of the formula VI can be obtained, for example, by conventional methylation [for example by esterification according to process variant d] of the free acid (VIA) which can be obtained by the oxidation process described above from the triol (IXA) of the pregnane series.

The removal of a protecting group from the 11$\beta$-hydroxy according to the invention in accordance with process variant (f) is carried out in a manner known per se, taking into account the specific requirements of the particular protecting group. Suitable for the protection of the 11$\beta$-hydroxy group in the context of the present invention are, for example, ester groups (acyl groups) that can be readily removed, such as formyl, chloroacetyl and, especially, trifluoroacetyl, or, especially, ether groups that can be readily removed, especially a tri(alkyl or aryl)silyl group, preferably a tri(lower alkyl)silyl group, such as the trimethylsilyl or tert.-butyldimethylsilyl group.

As is known, the removal of the ester groups takes place especially readily under solvolytic, for example alcoholytic or hydrolytic, conditions using mild basic agents, such as alkali metal or alkaline earth metal salts of weak inorganic acids (for example bicarbonates, especially sodium or potassium bicarbonate) or organic carboxylic acids (for example formates or acetates, especially potassium formate or potassium acetate), or, alternatively, using heteroaromatic bases, for example pyridine or collidine, in a suitable medium, for example an alcoholic medium, such as a methanolic medium, or an aqueous-alcoholic medium. A preferred method for solvolysis of the 11-trifluoroacetoxy group is described, for example, in German Patent Specification No. 1 593 519 in which the esterified hydroxy group in the 17$\alpha$-position remains intact; the operation is carried out as follows: the 11$\beta$-trifluoroacetoxy compound is treated in a lower alkanol with the salt of an acid having a $pK_a$ value in the range of from approximately 2.3 to approximately 7.3, such as an alkali metal azide (for example sodium or potassium azide) or an alkali metal formate (for example sodium or potassium formate), it being possible for this salt to be present only in catalytic amounts. It is also possible to remove the 11$\beta$-trifluoroacetyl group by treatment with silica gel according to the process described in German Offenlegungsschrift 2 144 405.

These ester groups that can be readily removed are advantageously introduced into the starting materials already in the relatively early preliminary stages of synthesis, especially in compounds of the pregnane series before the oxidative degradation of the hydroxyacetyl side chain; the introduction is carried out in a manner known per se, especially by acylation with a corresponding anhydride, such as trifluoroacetic anhydride, chloroacetic anhydride or a mixed anhydride of formic acid and acetic acid, preferably in a heteroaromatic base, such as pyridine, and advantageously at a temperature that does not exceed room temperature.

The removal according to the invention of the 11-O-trialkylsilyl groups is carried out in a manner known per se, for example by hydrolysis with catalysis using slightly acidic agents and conditions under which the esterified hydroxy group in the 17$\alpha$-position and the methoxycarbonyl group in the 17$\beta$-position remain intact, for example by the action of trifluoroacetic acid in the presence of water in a water-miscible organic solvent, such as a lower alkanol, for example methanol, ethanol, isopropyl alcohol or tert.-butyl alcohol, or an ether, for example 2-methoxyethanol or 2-ethoxyethanol, tetrahydrofuran or dioxan, also by the action of aqueous oxalic acid in these solvents or, alternatively, of aqueous formic or acetic acid alone, at temperatures of approximately from 0° to 50°, preferably in the region of room temperature. This removal can be carried out especially also with fluoride ions, or with agents yielding fluoride ions, having high selectivity, for example with fluorides of quaternary bases, such as, especially, tetraethylammonium fluoride, according to a conventional general process; there may be used as solvents, for example, the above-mentioned lower alkanols and ethers, also, however, dimethylformamide and heteroaromatic bases of the pyridine type; the reaction temperature is customarily approximately from 0° to 50° C., especially in the region of room temperature.

Advantageously the 11$\beta$-hydroxy is protected by a trialkylsilyl group in an earlier stage of synthesis so that conversions can be carried out that might otherwise affect the free 11$\beta$-hydroxy group, such as, for example, acylation of the 17$\alpha$-hydroxy, especially under relatively energetic conditions. The introduction of the protecting group is carried out, for example, by treating a suitable compound containing free 11$\beta$-hydroxy with a trialkylsilyl halide, such as, especially, trimethylsilyl chloride or tert.-butyldimethylsilyl chloride, preferably in the presence of an organic base, such as, especially, diethylamine or piperidine, and, as reaction medium, in an ether, for example tetrahydrofuran, dioxan, 1,2-dimethoxyethane or 1,2-diethoxyethane or diethyl ether, or in a heteroaromatic base, for example pyridine or homologues thereof, at temperatures of approximately from 0° to 50° C., preferably at or below room temperaure. After the introduction of the protecting group, the desired conversions can be carried out, such as, especially, the acylation of 17$\alpha$-hydroxy, but also the hydrolytic freeing of an acylated 21-hydroxy group, the oxidative degradation of the hydroxyacetyl side chain, 1,2-dehydrogenation and/or esterification of the 17$\beta$-carboxy, all of which conversions can be carried out under conditions that leave the protecting group intact; it is known that this group is especially stable under basic conditions.

The direct starting material of the present process variant (f), an 11$\beta$-trialkylsilyloxy-6$\beta$-fluoro-9$\alpha$-chloro-16$\beta$-methyl-17$\alpha$-OCOR-3-oxo-androsta-1,4-diene-17$\beta$-carboxylic acid methyl ester (VIIIA) in which R has the meaning given above, can be obtained by various routes, for example, in a typical sequence, as follows: 21-acetoxy-6$\alpha$-fluoro-9$\alpha$-chloro-11$\beta$,17$\alpha$-dihydroxy-16$\beta$-methylpregna-1,4-diene-3,20-dione is treated with a trialkylsilyl chloride under basic conditions (only the 11$\beta$-hydroxy being selectively etherified) and in the resulting protected intermediate, in succession, the acetylated 21-hydroxy is freed by mild basic hydrolysis, the hydroxyacetyl side chain is cleaved with periodic acid, the free 17α-hydroxy is acylated (preferably with basic catalysis) and the 17β-carboxy is esterified (for example with diazomethane). The same starting material (VIIIA) can be obtained also by a different advantageous route, which, at the same time, is a supplementary alternative to process variant (e), as folows: first of all a trialkylsilyl protecting group is introduced into 6α-fluoro-9α-chloro-11β, 17α-dihydroxy-16β-methyl-3-oxo-androsta-1,4-diene-17β-carboxylic acid methyl ester (VI) under the conditions described above, then the 17α-hydroxy is acylated according to process variant (e) and finally the protecting group is removed according to the present process variant (f).

The direct starting materials for all the process variants a–f, that is to say compounds II to VI and VIII, can be obtained from known, analogously substituted precursors of the pregnane series not only by the synthesis sequences specifically described above but also by other advantageous combinations of the oxidative degradation of the hydroxyacetyl side chain and the general processes described under a–f. In all these conversions and in the processes according to the invention described above themselves, it is preferable to use reagents and intermediates that result in the end products and intermediates given special mention, especially the end products and intermediates that are specifically mentioned.

Throughout the entire description, unless specifically defined, the term "lower" in connection with a hydrocarbon radical refers to a hydrocarbon radical having not more than 7 carbon atoms.

The invention relates also to those forms of the above processes in which a compound obtainable as an intermediate at any stage is used as starting material and the remaining steps are carried out or in which a starting material is formed under the reaction conditions.

The present invention relates also to pharmaceutical compositions and preparations for humans and mammals, which contain as active ingredient a therapeutically effective amount of the novel compounds of the formula A described above together with a pharmaceutical carrier and to their manufacture. There are used as carriers organic or inorganic substances that are suitable above all for topical administration or administration by inhalation, for example in the form of an aerosol, micropulverised power or a finely sprayed solution. Suitable for the formation thereof are substances that do not react with the novel compounds, such as, for example, water, gelatine, lactose, starch, magnesium stearate, talc, vegetable oils, benzyl alcohol, gums, polyalkylene glycols, petroleum jelly, cholesterol and other known carriers for medicaments. The pharmaceutical preparations and compositions can be especially in liquid or semi-liquid form as solutions, suspensions, emulsions, ointments or creams. If desired, these pharmaceutical preparations are sterilised and/or contain adjuncts, such as preservatives, stabilisers, wetting agents or emulsifiers. They may also contain additional therapeutically valuable or biologically active substances.

According to the invention, there come into consideration especially topically administrable pharmacuetical preparations, such as creams, ointments, pastes, foams, tinctures and solutions that contain from approximately 0.001 to approximately 0.5%, preferably from approximately 0.005 to approximately 0.05%, active ingredient.

Creams are oil-in-water emulsions that contain more than 50% water. There are used as oily base especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example petroleum jelly (petrolatum) or paraffin oil. Suitable as emulsifiers are surface-active substances having predominantly hydrophilic properties, such as corresponding non-ionic emulsifiers, for example fatty acid esters of polyalcohols or ethylene oxide adducts thereof, such as polyglycerine fatty acid esters or polyoxyethylenesorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl alcohol or stearyl alcohol. Additives to the aqueous phase are, inter alia, agents that reduce the drying-out of the cream, for example polyalcohols, such as glycerine, sorbitol, propylene glycol and/or polyethylene glycols, also preservatives and perfumes.

Ointments are water-in-oil emulsions that contain up to 70%, but preferably from approximately 20% to approximately 50%, water or aqueous phase. Suitable as the fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerine, propylene glycol, sorbitol and/or polyethylene glycol, and also preservatives and perfumes.

Fatty ointments are anhydrous and contain as base especially hydrocarbons, for example paraffin, petroleum jelly and/or liquid paraffins, also natural or partially synthetic fats, for example coconut fatty acid triglyceride, or preferably hardened oils, for example hydrogenated groundnut or castor oil, also fatty acid partial esters of glycerine, for example glycerine mono- and di-stearate, and also, for example, the fatty alcohols increasing the water-absorption capacity, emulsifiers and/or additives mentioned in connection with the ointments.

Pastes are creams and ointments having secretion-absorbing powder constituents, such as metal oxides, for example titanium dioxide or zinc oxide, also talc and/or aluminium silicates, the purpose of which is to bind any moisture or secretions present.

Tinctures and solutions generally have an aqueous-ethanolic base to which are added, inter alia, polyalcohols, for example glycerine, glycols and/or polyethylene glycol, as humectants for reducing evaporation, and fat-restoring substances, such as fatty acid esters with lower polyethylene glycols, that is to say lipophilic substances that are soluble in the aqueous mixture, as a replacement for the fatty substances removed from the skin by the ethanol, and, if necessary, other adjuncts and additives.

Suitable pharmaceutical compositions for administration by inhalation of aerosols or sprays are, for example, solutions, suspensions or emulsions of the active ingredient of the formula A according to the invention with a suitable pharmaceutically acceptable solvent, such as, especially, ethanol and water, or a mixture of such solvents. They may, if necessary, also contain other pharmaceutical adjuncts, such as non-ionic or anionic surface-active agents, emulsifiers and stabilisers, and also active ingredients of a different type, and, especially, are advantageously mixed with a propellant gas, such as an inert gas under elevated pressure or, especially, with a readily volatile liquid that boils preferably under normal atmospheric pressure below customary room temperature (for example approximately from −30 to +10°), such as a polyhalogenated lower alkane that is at least partially fluorinated, or with a mixture of such liquids. Such pharmaceutical compositions, which are used for the most part as intermediates or supply mixtures for the manufacture of corresponding medicaments in finished form, contain the active ingredient customarily in a concentration of from approximately 0.01 to approximately 5, especially from approximately 0.1 to approximately 1%, by weight. For the manufacture of medicaments in finished form, such a pharmaceutical composition is introduced into suitable containers, such as phials and pressurised bottles, which are provided with a spraying device or valve suitable for this purpose. The valve is preferably designed as a dosing valve which, when actuated, releases a pre-determined amount of the liquid corresponding to a pre-determined dose of the active ingredient. When manufacturing the finished form of medicament, it is also possible to introduce corresponding amounts of the pharmaceutical composition in the form of the supply solution and the propellant separately into the containers.

Foams are administered from pressurised containers and are liquid oil-in-water emulsions in aerosol form; halogenated hydrocarbons, such as chlorofluoro-lower alkanes (for example dichlorodifluoromethane and dichlorotetrafluoroethane) are used as propellants. There are used as the oily phase, inter alia hydrocarbons, for example paraffin oil, fatty alcohols, for example cetyl alcohol, fatty acid esters, for example isopropyl myristate, and/or other waxes. There are used as emulsifiers, inter alia mixtures of emulsifiers having predominantly hydrophilic properties, such as polyoxyethylenesorbitan fatty acid esters (Tweens), and emulsifiers with predominantly lipophilic properties, such as sorbitan fatty acid esters (Spans). The customary additives, such as preservatives, are also added.

The manufacture of the topically administrable pharmaceutical compositions and preparations is carried out in a manner known per se, for example by dissolving or suspending the active ingredient in the base or, if necessary, in a part thereof. When processing the active ingredient as a solution, it is generally dissolved in one of the two phases before emulsification; when processing the active ingredient as a suspension it is mixed with part of the base after emulsification and then added to the rest of the formulation.

The dosage of the active ingredient, for example of the compounds given special emphasis above, is in principle determined in a manner analogous to that for recognised topical anti-inflammatory agents of the corticoid type, including inhalation preparations; it also depends, however, on the one hand on the species, weight, age and individual condition of the warm-blooded animal and, on the other hand, on the method of administration; a suitable dose for each individual case can be determined in known manner in a routine test.

The invention relates also to a method for alleviating or relieving pathological inflammatory conditions of the body and, especially, of the skin of a warm-blooded animal, especially humans, which is characterised by treating the body or part of the body, preferably by topical administration, with an anti-inflammatorily effective amount of a compound of the formula A alone or in the form of a pharmaceutical preparation. The term "an anti-inflammatorily effective amount" is to be understood as meaning an amount of the active ingredient that is sufficient to bring about significant inhibition of the inflammation.

The invention relates also to the use of the active ingredients of the formula A according to the invention for alleviating or relieving pathological allergic conditions and/or symptoms of the body of mammals, especially humans, which occur especially in the case of asthma. This use or the corresponding therapeutic method is characterised by treating the affected body or part of the body with an anti-allergically effective amount of a compound of the formula A alone or in the form of a medicament, especially in the form of a pharmaceutical composition designed for inhalation. The term "an anti-allergically effective amount" is to be understood as meaning an amount of the active ingredient that is sufficient to bring about significant relief of the allergic reaction, such as bronchocontraction.

The following Examples illustrate in detail a practical method for carrying out the invention, without limiting the scope of the invention. Hereinbefore an hereinafter, the temperatures are given in degress Centigrade; unless specifically indicated, solvent mixtures are give in % by volume or in volume:volume ratio, and solutions of solids are given in % by weight, that is to say as weight of the solid (in g) in parts by volume (in ml) of the solution.

EXAMPLE 1

While stirring, a solution of 1.340 g of 9$\beta$,11$\beta$-epoxy-6$\alpha$-fluoro-17$\alpha$-hydroxy-16$\beta$-methyl-3-oxo-androsta-1,4-diene-17$\beta$-carboxylic acid methyl ester 17-propionate in 66 ml of chloroform is saturated at usual temperature with dry hydrogen chloride. After the mixture has been left to act for 4 hours, it is diluted with 200 ml of methylene chloride and extracted by shaking in succession with 100 ml of freshly prepared 1M ammonium bicarbonate solution, twice with 40 ml of 0.5M ammonium bicarbonate solution each time and 5 times with 40 ml of water each time. The organic phases are combined, dried with sodium sulphate, filtered and concentrated by evaporation in vacuo, while adding ether several times towards the end. Approximately 1.5 g of crystalline crude product are obtained which are dissolved in 50 ml of methylene chloride and purified over a column, prepared in methylene chloride, of 250 g of silica gel (0.063–0.200 mm, deactivated with 10% water) using methylene chloride/ethyl acetate mixtures having an increasing ethyl acetate content. From the portions which have been eluted with methylene chloride/ethyl acetate (95:5) and are uniform in thin-layer chromatography there are obtained, by crystallisation from ether, 1.12 g of pure 9$\alpha$-chloro-6$\alpha$-fluoro-11$\beta$,17$\alpha$-dihydroxy-16$\beta$-methyl-3-oxo-androsta-1,4-diene-17$\beta$-carboxylic acid methyl ester 17-propionate having a melting point of 222°–224°.

The 9β,11β-epoxy-6α-fluoro-17α-hydroxy-16β-methyl-3-oxo-androsta-1,4-diene-17β-carboxylic acid methyl ester 17-propionate used as starting material can be manufactured as follows:

(a) A solution of 19.50 g of 9β,11β-epoxy-6α-fluoro-17α,21-dihydroxy-16β-methylpregna-1,4-diene-3,20-dione [see C.A. 97 (11), 092636, Registry No. 82662-44-0, obtainable also from the corresponding 17,21-diacetate, see U.S. Pat. No. 4,346,037, by hydrolysis with potassium carbonate in aqueous methanol] and 1.0 g of p-toluenesulphonic acid in 100 ml of dimethylformamide and 25 ml of ortho-propionic acid triethyl ester is stirred for 4 hours at 20°–23°, 8.2 ml of pyridine are then added to the solution and the reaction mixture is diluted with 3000 ml of methylene chloride and extracted by shaking with 5×200 ml of water and, with back extraction, with 5×200 ml of methylene chloride. The methylene chloride solution collected is dried with sodium sulphate, filtered and concentrated by evaporation, ether being added several times towards the end. The almost colourless crystalline residue of 9β,11β-epoxy-6β-fluoro-17α, 21-dihydroxy-16β-methylpregna-1,4-diene-3,20-dione 17,21-(ethyl ortho-propionate) is further processed without being purified.

(b) The crude product obtained (23.4 g) is taken up in 3600 ml of ethanol; a solution of 12.60 g of oxalic acid dihydrate in 200 ml of ethanol and 200 ml of water is added and the whole is stirred for 20 hours at 20°–23°. The reaction solution is then cooled to 0°–3° and, while stirring, 1700–1750 ml of 0.1N potassium bicarbonate solution are added dropwise until the pH is 5.0–5.5. The reaction mixture is then concentrated in vacuo to a residual volume of approximately 1000 ml and the hydrolysis product that has separated out is taken up in a total of 3600 ml of methylene chloride. The extract, washed with a total of 1200 ml of 0.1N ammonium bicarbonate solution and 1200 ml of water, is dried with sodium sulphate, filtered and concentrated by evaporation. The resulting crude product is dissolved in 62.5 ml of methylene chloride to separate off the 21-monopropionate that has also formed and after absorption onto a column, prepared in methylene chloride, of 2500 g of silica gel (0.063–0.200 mm, deactivated with 10 % water) is chromatographed. Elution with 3750 ml each of toluene/ethyl acetate mixture (75:25), (70:30), (65:35) and (60:40) yields a total of 19.3 of the more strongly polar component. Recrystallisation from ether using methylene chloride as solubiliser yields 18.15 g of pure 9β,11β-epoxy-6α-fluoro-17α, 21-dihydroxy-16β-methylpregna-1,4-diene-3,20-dione 17-propionate having a melting point of 180°–182°.

(c) 40 ml of saturated methanolic copper(II) acetate solution are added to a solution of 4.465 g of 9β,11β-epoxy-6α-fluoro-17α,21-dihydroxy-16β-methylpregna-1,4-diene-3,20-dione 17-propionate in 160 ml of methanol and, while stirring, oxygen is passed through the solution. After 2 ½ hours, 80 ml of a 0.05M solution of the disodium salt of ethylenediaminetetraacetic acid in water are added and the whole is concentrated in vacuo to a residual volume of approximately 80 ml. While adding a total of 180 ml of water, the methanol is removed in vacuo at a bath temperature of 45°–50° so that no residue remains, with final concentration of the mixture to a volume of approximately 50 ml. After standing at 0° and after being crushed with a glass rod, the crystalline product is collected on a suction filter, washed out with ice-cold water and dried at usual temperature over calcium chloride. In this manner, 4.60 g of 9β,11β-epoxy-6α-fluoro-17α-hydroxy-16β-methyl-3,20-dioxopregna-1,4-dien-21-al-17-propionate are obtained having a melting point of 94°–96°.

(d) 100 ml of methylene chloride are poured over 4.60 g of 9β,11β-epoxy-6α-fluoro-17α-hydroxy-16β-methyl-3,20-dioxopregna-1,4-diene-21-al-17-propionate and while excluding moisture under an argon atmosphere 10 g of 3-chloroperbenzoic acid are added. After stirring for 8 hours at usual temperature, thin-layer chromatography reveals no further educts. The yellow solution is diluted with 400 ml of ether and 1500 ml of methylene chloride/ether (1:4), approximately 100 g of ice are added and then the excess oxidising agent is destroyed by shaking with 600 ml of ice-cold 0.2M sodium iodide solution, 120 ml of 1N acetic acid and 600 ml of 0.2M sodium thiosulphate solution. The whole is then washed with saturated sodium sulphate solution. The aqueous extracts are subsequently extracted with a (1:4) mixture of methylene chloride/ether and the organic phase is combined with the main solution. After drying with sodium sulphate and filtration, the whole is concentrated to a residual volume of approximately 400 ml, the concentrate is cooled to 0°–3° and an ice-cold approximately 0.5M ethereal diazomethane solution (total approximately 140 ml) is added until the pale yellow colouring remains constant for 30 minutes. Concentration by evaporation under reduced pressure yields an oily residue which is dissolved in 125 ml of toluene and chromatographed over a column, prepared in toluene, of 500 g of silica gel (0.063–0.200 mm, deactivated with 10% water). Elution with (97.5:2.5) and (90:10) mixtures of toluene/ethyl acetate and crystallisation from ether of the pure portions collected with methylene chloride/ether mixtures yield a total of 2.70 g of 9β,11β-epoxy-6α-fluoro-17α-hydroxy-16β-methyl-3-oxo-androsta-1,4-diene-17β-carboxylic acid methyl ester 17-propionate having a melting point of 203°–205°. In analogous manner, it is also possible to obtain 17-acetates and 17-pivalates of the intermediates mentioned under a–e above.

EXAMPLE 2

75 ml of an approximately 0.5 M solution of diazomethane in ether are added slowly at 0°–3° to a solution of 3.00 g of 9α-chloro-6α-fluoro-11β,17α-dihydroxy-16β-methyl-3-oxo-androsta-1,4-diene-17β-carboxylic acid 17-propionate [crude product containing 3-chlorobenzoic acid; see below] in 250 ml of ether, the yellow colour remaining constant at the end. After a further ½ hour, the solution is concentrated by evaporation under reduced pressure, the oily residue is dissolved in a small amount of methylene chloride/toluene (1:1) and, while rinsing with toluene, is absorbed onto a column, prepared in toluene, of 180 g of silica gel (0.063–0.200 mm) and the column is eluted with toluene/ethyl acetate (4:1). A small first running which contains 60 mg of 9α-chloro-6β-fluoro-11β, 17α-dihydroxy-16β-methyl-3-oxo-androsta-1,4-diene-17β-carboxylic acid methyl ester 17-propionate that is epimeric in the 6-position and has a melting point of 214°–218° (from ether/petroleum ether) is followed by fractions of the main component. Concentration by evaporation and crystallisation of the residue from methylene chloride/ether yield the desired 9α-chloro6α-fluoro-11β,17α-dihydroxy-16β-methyl-3-oxo-androsta-1,4-diene-17β-carboxylic acid methyl ester 17-propionate having a melting point of 220°–222°, which is identical with the product of Example 1.

The 9α-chloro-6α-fluoro-11β,17α-dihydroxy-16β-methyl-3-oxo-androsta-1,4-diene-17β-carboxylic acid 17-propionate used as starting material can be manufactured as follows:

(a) 1.16 g of 9β,11β-epoxy-6α-fluoro-17α-hydroxy-16β-methyl-3, 20-dioxopregna-1,4-dien-21-al-17-propionate (see Example 1c) are dissolved in 25 ml of methylene chloride under a dry argon atmosphere and treated with 2.5 g of 3-chloroperbenzoic acid. After stirring for 8 hours at usual temperature, the solution is diluted with 200 ml of ether and 50 ml of methylene chloride, extracted while adding ice by shaking in succession with 150 ml of 0.2M sodium iodide solution, 30 ml of 1N acetic acid and 150 ml of 0.2M sodium thiosulphate solution and dried with sodium sulphate. Concentration by evaporation yields a crystalline residue which, in addition to 3-chloroperbenzoic acid, comprises substantially 9β,11β-epoxy-6α-fluoro-17α-hydroxy-16β-methyl-3-oxo-androsta-1,4-diene-17β-carboxylic acid 17-propionate.

(b) While stirring and while cooling to 0°–3°, dry hydrogen chloride is introduced over the surface of a solution of 3.4 g of the product mixture obtained as described above in 300 ml of chloroform. The reaction is monitored by thin-layer chromatography on silica gel plates using chloroform/methanol/water (89:10:1) and is generally complete after approximately 5 hours. The reaction mixture is diluted with 100 ml of chloroform, cooled with ice, adjusted to a pH of approximately 6 using 2N ammonium bicarbonate solution, washed with water, dried with sodium sulphate and concentrated by evaporation, ether being added several times towards the end. The resulting crystalline residue comprises, according to thin-layer analysis, more than 90 % 9α-chloro-6α-fluoro-11β,17α-dihydroxy-16β-methyl-3-oxo-androsta-1,4-diene-17β-carboxylic acid 17-propionate together with 3-chloroperbenzoic acid from the preceding stage. This product can be used in the esterification stage without being purified.

EXAMPLE 3

While excluding moisture, 3.6 ml of trifluoroacetic acid anhydride are added dropwise at approximately 15° to a stirred solution of 15 mg of p-toluenesulphonic acid in 16.4 ml of propionic acid and the mixture is stirred for a further 4 hours at room temperature. Under a dry argon atmosphere, this freshly prepared reagent solution is poured over 109 mg of 9α-chloro-6α-fluoro-11β,17α-dihydroxy-16β-methyl-3-oxo-androsta-1,4-diene-17β-carboxylic acid methyl ester and the whole is stirred for 4 hours at room temperature. (In this operation the starting material gradually dissolves and the product begins to separate out in the form of crystals). The reaction mixture is diluted with 80 ml of ethyl acetate and, while cooling with ice, is washed in succession with 100 ml of water, 30 ml of 1.25M sodium bicarbonate solution and 100 ml of water and the aqueous portions are subsequently extracted twice with 50 ml of ethyl acetate each time. The combined organic extracts are dried over sodium sulphate and concentrated by evaporation in vacuo, and the residue is dissolved in approximately 10 ml of methylene chloride and introduced into a column of 25 g of silica gel. Fractions obtained by elution with methylene chloride/ethyl acetate (4:1) yield, after removal of the solvent and recrystallisation from ether/petroleum ether, the desired 9α-chloro-6α-fluoro-11β, 17α-dihydroxy-16β-methyl-3-oxo-androsta-1,4-diene-17β-carboxylic acid methyl ester 17-propionate, m.p. 222°–223°, which is identical with the product of Example 1.

The starting material can be manufactured as follows:

(a) An oxidation reagent, which is prepared separately by dissolving 51.7 g of periodic acid dihydrate in 150 ml of water and 20 ml of pyridine and making up with water to a final total volume of 225 ml, is added while stirring to a solution of 9.76 g of 9β,11β-epoxy-6α-fluoro-17α, 21-dihydroxy-16β-methylpregna-1,4-diene-3,20-dione in 1000 ml of tetrahydrofuran. After being stirred for 17 hours at room temperature, the reaction mixture is diluted with 600 ml of water and concentrated to approximately 400 ml under a water-jet vacuum. The solid that has precipitated is collected on a suction filter, washed out with ice-cold water and dried at 20° under a high vacuum. The resulting crystalline 9β,11β-epoxy-6α-fluoro-17α-hydroxy-16β-methylandrosta-1,4-diene-17β-carboxylic acid can be further processed without being additionally purified.

(b) A total of 350 ml of an approximately 0.6M solution of diazomethane in ether is added in portions at 0°–3° to a solution of 5.80 g of the above acid in 500 ml of methanol until the solution remains yellowcoloured. After being stirred for a further hour at 0°–3°, the reaction solution is highly concentrated under a water-jet vacuum and the crystallisate is suspended in a small amount of ether and filtered with suction. Drying yields 9β,11β-epoxy-6α-fluoro-17α-hydroxy-16β-methylandrosta-1,4-diene-17β-carboxylic acid methyl ester in the form of slightly beige-tinged crystals, m.p. 207°–209°.

(c) While stirring under an argon atmosphere, 5.20 g of the above compound are dissolved in 400 ml of chloroform and, while stirring, dry hydrogen chloride is introduced over the surface of the solution at 0°–3°. The progress of the reaction is monitored by thin-layer chromatography [silica gel plate; eluant: toluene/ethyl acetate (1:9)] until the reaction is complete after approximately 3–3.5 hours. The reaction mixture is washed in succession twice with 400 ml of ice-cold water each time, once with 200 ml of 1.25 M sodium bicarbonate solution and twice with 300 ml of ice-cold water each time and each of the aqueous extracts is subsequently extracted with 200 ml of chloroform. The combined organic phase is dried over sodium sulphate, concentrated to approximately 300 ml and, while rinsing with methylene chloride, is introduced into a column of 700 ml of silica gel. Elution with toluene/ethyl acetate (1:3), conventional working up of the fractions and recrystallisation from hexane/ether yield 9α-chloro-6α-fluoro-11β,17α-dihydroxy-16 β-methyl-3-oxo-androsta-1,4-diene-17β-carboxylic acid methyl ester, m.p. 228°–229° (after conversion of the crystalline form at 199°–203°).

EXAMPLE 4

While stirring, 0.25 ml of 0.5N aqueous perchloric acid and, dropwise, 0.13 ml of tert.-butyl hypochlorite are added in succession to a solution, prepared under argon and cooled to −10 to −12°, of 107.7 mg of 6α-fluoro-17α-hydroxy-16β-methyl-3-oxo-androsta-1,4,9(11)-triene-17β-carboxylic acid methyl ester 17-propionate in 2.3 ml of acetone and the whole is stirred for 1 hour at 0°–3°, poured into an ice-cold mixture of 0.30 ml of 0.5M sodium bicarbonate solution and 20 ml of water and concentrated to approximately 5 ml at approximately 2.5 mbar. The reaction product is taken up in a mixture of methylene chloride/ether (1:2), the solution is washed while ice-cold with 10 ml of a (0.1M sodium iodide +0.1N sulphuric acid) solution, with 10 ml of 0.1N sodium thiosulphate, twice with 10 ml of ammonium bicarbonate solution each time and with water and the aqueous extracts are then extracted with the same mixture of solvents. The organic phase collected is dried over sodium sulphate and concentrated under reduced pressure. Recrystallisation from methylene chloride/ether yields 9α-chloro-6α-fluoro-11β,17α-dihydroxy-16β-methyl-3-oxo-androsta-1,4-diene-17β-carboxylic acid methyl ester 17-propionate, m.p. 219°–222°, which is identical with the product of Example 1.

The starting material can be manufactured, for example, as follows:

A solution of 1.90 g of 9β,11β-epoxy-6α-fluoro-17α-hydroxy-16β-methyl-3-oxo-androsta-1,4-diene-17β-carboxylic acid methyl ester 17-propionate [see Example 1d)] in 75 ml of tetrahydrofuran and 8.5 ml of 65% hydriodic acid is stirred for 12 hours at 40°–43°, cooled to approximately 5° and diluted with 500 ml of ethyl acetate. To remove the iodine that has separated out, the reaction mixture is extracted by shaking with an ice-cold mixture of 400 ml of 0.4N sodium thiosulphate solution and 80 ml of 2N acetic acid and then washed with 400 ml of ice-cold water, 160 ml of ice-cold 1.25M sodium bicarbonate solution and again with 400 ml of ice-cold water, the extracts subsequently being extracted in sequence twice with 200 ml of ethyl acetate each time. The combined organic phase, dried with sodium sulphate, is concentrated by evaporation in vacuo and the crude product is chromatographed on a column of 250 g of silica gel; elution with mixtures of toluene/ethyl acetate (95:5) and (80:20), conventional working up of the fractions and recrystallisation from ether/petroleum ether yields the desired 6α-fluoro-17α-hydroxy-16β-methyl-3-oxo-androsta-1,4,9(11)-triene-17β-carboxylic acid methyl ester 17-propionate, m.p 164°–165°.

EXAMPLE 5

While stirring under argon, a solution of 607 mg of 9α-chloro-6α-fluoro-11β,17α-dihydroxy-16β-methyl-3-oxo-androst-4-ene-17β-carboxylic acid methyl ester 17-propionate and 1.58 g of 2,3-dichloro-5,6-dicyano-1,4-benzoquinone in 15 ml of peroxide-free dioxan is heated at 100° for 60 hours in a pressure vessel. After cooling, the mixture is poured into 125 ml of water, rinsed with approximately 35 ml of dioxan and freed of dioxan by concentration under a high vacuum at a bath temperature of 27°–30° to a residual volume of approximately 20 ml. The mixture is made into a slurry in 100 ml of water and extracted in succession with 250, 100 and 100 ml of a mixture of methylene chloride/ether (1:2). The extracts are washed three times with 50 ml of ice-cold 2N sodium carbonate solution each time and five times with 50 ml of water each time and the combined organic solutions are dried with sodium sulphate and concentrated by evaporation in vacuo. The residue is purified by conventional preparatory thin-layer chromatography over silica gel using cyclohexane/ethyl acetate (1:1) as eluant and crystallised from ether. 9α-chloro-6α-fluoro-11β,17α-dihydroxy-16β-methyl-3-oxo-androsta-1,4-diene-17β-carboxylic acid methyl ester 17-propionate is obtained, m.p. 221°–224°, which is identical with the product of Example 1.

The starting material can be manufactured in a manner analogous to that described in detail in Example 1 for the corresponding 1,4-dienes, starting from 9β,11β-epoxy-6α-floro-17α,21-dihydroxy-16β-methylpregn-4-ene-3,20-dione via the corresponding 1,2-saturated intermediates.

EXAMPLE 6

While stirring and excluding moisture, 2.3 ml of trifluoroacetic acid-anhydride are added dropwise at 15° to a solution of 17 mg of p-toluenesulphonic acid in 6.0 ml of glacial acetic acid and the mixture is left to stand overnight. 5.0 ml of this reagent solution are added under a dry argon atmosphere to a solution of 533 mg of 9α-chloro-6α-fluoro-11β,17α-dihydroxy-16β-methyl-3-oxo-androsta-1,4-diene-17β-carboxylic acid methyl ester (for manufacture see Example 3a–c) in 5.0 ml of methylene chloride and the whole is stirred for 3 hours at room temperature. The reaction mixture is poured into 60 ml of ice-cold water and extracted with two portions each of 80 ml of ethyl acetate. While cooled with ice, these extracts are washed separately in succession with 80 ml of water, twice with 50 ml of 1.25M sodium bicarbonate solution each time and twice with 50 ml of water each time, combined, dried with sodium sulphate and concentrated by evaporation in vacuo. Crystallisation of the residue from acetone yields 9α-chloro-6α-fluoro-11β,17α-dihydroxy-16β-methyl-3-oxo-androsta-1,4-diene-17β-carboxylic acid methyl ester 17-acetate, m.p. 242°–243°. A further amount of the product can be obtained by conventional chromatography of the mother liquors, for example over silica gel using toluene/ethyl acetate (9:1) as eluant.

Example 7

While stirring and excluding moisture, 2.3 ml of trifluoroacetic acid anhydride are added dropwise at 15° to a solution of 17 mg of p-toluenesulphonic acid in 10.8 ml of valeric acid and the mixture is left to stand for 24 hours at room temperature. Under a dry argon atmosphere, 5.0 ml of this reagent solution are added to a solution of 533 mg of 9α-chloro-6α-fluoro-11β,17α-dihydroxy-16β-methyl-3-oxo-androsta-1,4-diene-17β-carboxylic acid methyl ester (for manufacture see Example 3a–c) in 5.0 ml of methylene chloride and the whole is stirred for 3 hours at room temperature. The reaction mixture is extracted wth 125 ml of ethyl acetate, cooled to 0°–3° and, while ice-cold, is washed in succession three times with 50 ml of 2N sodium carbonate solution each time and three times with 50 ml of water each time. The aqueous extracts are then extracted with 75 ml of ethyl acetate and the combined organic extracts are dried with sodium sulphate and concentrated by evaporation in vacuo. Chromatography over a column of 130 g of silica gel, elution with toluene/ethyl acetate (2:1), conventional working up of the eluates and crystallisation of the product from methylene chloride/ether yield 9α-chloro6α-fluoro-11β,17α-dihydroxy-16β-methyl-3-oxo-androsta-1,4-diene-17β-carboxylic acid methyl ester 17-valerate, m.p. 201°–202°.

EXAMPLE 8

An ointment containing 0.1% 6α-fluoro-9α-chloro-11β-hydroxy-16β-methyl-17α-propionyloxy-3-oxo-androsta-1,4-diene-17β-carboxylic acid methyl ester can be manufactured as follows:
Composition
  6α-fluoro-9α-chloro-11β-hydroxy-16β-methyl-17α-propionyloxy-3-oxo-androsta-1,4-diene-17β-carboxylic acid methyl ester: 0.1%
  petroleum jelly: 45.0% paraffin oil: 19.6%
cetyl alcohol: , 5.0%
beeswax: 5.0%
sorbitan sesquioleate: 5.0%
p-hydroxybenzoic acid ester: 0.2%
perfume: 0.1%
water: 20.0%

The fatty substances and the emulsifiers are melted together. The preservative is dissolved in water and the solution is emulsified into the fatty melt at elevated temperature. After cooling, a suspension of the active ingredient in a portion of the fatty melt is worked into the emulsion and finally the perfume is added.

EXAMPLE 9

An inhalation solution containing a propellant, forming an aerosol of solid matter and containing 0.1% by weight active ingredient (for example the 17-propionate according to Example 1).

| Composition: | % by weight |
| --- | --- |
| active ingredient, micronised | 0.1 |
| sorbitan trioleate | 0.5 |
| propellant A (trichlorotrifluoroethane) | 4.4 |
| propellant B (dichlorodifluoromethane and | 15.0 |
| 1,2-dichlorotetrafluoroethane) | 80.0 |

Manufacture

While excluding moisture and using a customary homogeniser, the active ingredient is dissolved in trichlorotrifluoroethane while adding sorbitan trioleate and introduced into an aerosol container provided with a dosing valve; the container is sealed and filled under pressure with propellant B.

I claim:

1. Compounds of the formula

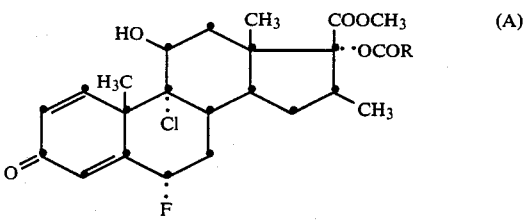

in which R represents alkyl having from 1 to 4 carbon atoms.

2. A compound of the formula (A) according to claim 1 in which R is a linear alkyl radical.

3. A compound according to claim 1 which is 9α-chloro-6α-fluoro-11β-hydroxy-16β-methyl-3-oxo-17α-propionyloxyandrosta-1,4-diene-17β-carboxylic acid methyl ester.

4. A compound according to claim 1 which is 9α-chloro-6α-fluoro-11β-hydroxy-16β-methyl-3-oxo-17α-acetoxyandrosta-1,4-diene-17β-carboxylic acid methyl ester.

5. A compound according to claim 1 which is 9α-chloro-6α-fluoro-11β-hydroxy-16β-methyl-3-oxo-17α-valeryloxyandrosta-1,4-diene-17β-carboxylic acid methyl ester.

6. A pharmaceutical composition containing an effective anti-inflammatory amount of a compound according to claim 1 and a pharmaceutically acceptable carrier.

7. A method of treating an inflammatory condition in a warm-blooded animal in need of such treatment, comprising administering an effective anti-inflammatory amount of a compound according to claim 1 to said animal.

* * * * *